US006380244B2

(12) United States Patent
Martin et al.

(10) Patent No.: US 6,380,244 B2
(45) Date of Patent: *Apr. 30, 2002

(54) NUTRITIONAL AND THERAPEUTIC USES OF 3-HYDROXYALKANOATE OLIGOMERS

(75) Inventors: David P. Martin; Oliver P. Peoples, both of Arlington; Simon F. Williams, Sherborn; Luhua Zhong, Quincy, all of MA (US)

(73) Assignee: Metabolix, Inc., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/359,086

(22) Filed: Jul. 22, 1999

Related U.S. Application Data
(60) Provisional application No. 60/093,760, filed on Jul. 22, 1998.

(51) Int. Cl.$^7$ ........................ A61K 31/335; A61K 47/00
(52) U.S. Cl. ........................ 514/449; 514/450; 514/452; 514/460; 514/473; 514/546; 514/547; 514/509; 424/438; 424/439; 424/442
(58) Field of Search ................................. 514/546, 450, 514/449, 452, 547, 460, 473, 909; 424/438, 439, 442

(56) References Cited

U.S. PATENT DOCUMENTS

| 4,329,359 A | | 5/1982 | Stahly |
| 4,365,088 A | * | 12/1982 | Vanlautem et al. ......... 562/579 |
| 4,423,072 A | | 12/1983 | Stahly |
| 4,563,354 A | | 1/1986 | Chang et al. |
| 5,093,044 A | | 3/1992 | Wretlind et al. |
| 5,126,373 A | * | 6/1992 | Brunengraber et al. ..... 514/547 |

FOREIGN PATENT DOCUMENTS

| EP | 0 316 993 A1 | 5/1989 |
| EP | 0321428 A1 | 6/1989 |
| EP | 0 780 123 A1 | 6/1997 |
| JP | 6/321778 | 11/1994 |
| WO | WO 88/08301 A1 | 11/1988 |
| WO | WO 90/02548 A1 | 3/1990 |
| WO | WO 90/02549 A1 | 3/1990 |
| WO | WO 90/11753 A1 | 10/1990 |
| WO | WO 95/09144 A1 | 4/1995 |
| WO | WO 95/18781 A1 | 7/1995 |
| WO | WO 97/15681 A1 | 5/1997 |
| WO | WO 98/41200 A1 | 9/1998 |
| WO | WO 98/41201 A1 | 9/1998 |
| WO | WO 99/34687 A1 | 7/1999 |

OTHER PUBLICATIONS

Beylot, et al., "Metabolic effects of a D–beta–hydroxybutyrate infusion in septic patients: inhibition of lipolysis and glucose production but not leucine oxidation," *Crit. Care Med.* 22(7):1091–98 (1994).

Birkhahn & Border, "Intravenous feeding of the rat with short chain fatty acid esters. II. Monoacetoacetin," *Am. J. Clin. Nutr.* 31(3):436–41 (1978).

Birkhaun, et al., "Monoglyceryl acetoacetate: a ketone body–carbohydrate substrate for parenteral feeding of the rat," *J. Nutr.* 109(7):1168–74 (1979).

Desrochers, et al., "R,S–1,3–butanediol acetoacetate esters, potential alternates to lipid emulsions for total parental nutrition," *Nutr. Biochem.* 6:111–18 (1995).

Lammerant, et al., "Inhibitory effects of the D(–)isomer of 3–hydroxybutyrate on cardiac non–esterified fatty acid uptake and oxygen demand induced by norepinephrine in the intact dog," *J. Mol. Cell Cardiol.* 17(4):421–33 (1985).

Müller, et al., "Bildung 12–bis 40–gliedriger oligolide aus enantiomerenreinen 3–Hydroxybuttersäure–Derivaten–Bausteine für eine $2_1$–und eine $3_1$ –Helix," *Chimia* 45:376–79 (1991).

Pawan & Semple, "Effect of 3–hydroxybutyrate in obese subjects on very–low–energy diets and during therapeutic starvation," *Lancet.* 1(8314–5):15–17 (1983).

Riis & Mai, "Gas chromatographic determination of poly–β–hydroxybutyric acid in microbial biomass after hydrochloric acid propanolysis," *J. Chromatography* 445:285–89 (1988).

(List continued on next page.)

*Primary Examiner*—Frederick Krass
(74) *Attorney, Agent, or Firm*—Holland & Knight LLP

(57) ABSTRACT

Nutritional or therapeutic compositions are provided for increasing ketone body levels in the blood of mammals by providing a source of ketone bodies in the form of linear or cyclic oligomers and/or derivatives of 3-hydroxyacids. The 3-hydroxyacid can be in the form of a linear oligomer of 3-hydroxyacids other than linear homo-oligomers of 3-hydroxybutyric acid if administered in combination with acetoacetate, cyclic oligomers of 3-hydroxyacids, esters of the linear or cyclic oligomers, esters of 3-hydroxyacids other than 3-hydroxybutyric acid, and combinations thereof. An oligomer generally refers to a polymer of three or more hydroxyacids. Preferred 3-hydroxyacids include 3-hydroxybutyrate, 3-hydroxyvalerate, 3-hydroxyhexanoate, and 3-hydroxyheptanoate. Oligomers of odd-carbon number 3-hydroxyacids such as 3-hydroxyvalerate have advantages since they have a higher energy content than oligomers of 3-hydroxyacids having an even-number of carbons. The cyclic oligomers have advantageous properties since they result in a sustained, and/or controlled, ketone blood level over a period of hours. The compositions can be administered orally, for example, as a nutritional or dietary supplement, or intravenously. Increasing blood ketone levels is useful for seizure control, metabolic disease control, reduction of protein catabolism, appetite suppression, parenteral nutrition, increasing cardiac efficiency, treatment of diabetes and insulin resistant states, and treatment of effects of neurodegenerative disorders and epilepsy.

12 Claims, 1 Drawing Sheet

OTHER PUBLICATIONS

Seebach, et al., "187. On the macrolactonization of β–Hydroxy Acids, Crystal structures of the pentolide and the hexolide from (R)–3–Hydroxybutanoic acid. Molecular modeling studies of the tetrolide," *Helv. Chim. Acta.* 72:1704–17 (1989).

Seebach, et al., "The triolide of (R)–3–Hydroxybutyric acid–Direct preparation form polyhydroxybutyrate and formation of a crown estercarbonyl complex with Na Ions," *Angew Chem. Int. Eng. Ed.* 4:434–35 (1992).

Seebach, et al., "18. High–yield synthesis of 20–, 24–, and 28–membered macropentolide, –hexolide, and –heptolide, respectively, from (R)–or (S)–3–Hydroxybutanoic acid under Yamaguchi's Macrolactonization Conditions[1])" *Helv. Chim. Acta.* 71:155–67 (1988).

Steinbuchel & Valentin, "Diversity of bacterial polyhydroxyalkanoic acids," *FEMS Microbiol. Lett.* 128:219–28 (1995).

Steinbuchel, et al., "Synthesis and production of poly(3–hydroxyvaleric acid) homopolyester by *Chromobacterium violaceum*," *Appl. Microbiol. Biotechnol.* 39:443–49 (1993).

Williams, et al., "Biodegradable plastics from plants," *CHEMTECH* 26:38–44 (1996).

Brown, et al., "Monitoring beta–hydroxybutyrate as an anticonvulsant level in the ketogenic diet," *Epilepsia* 39:168–69 (1998).

Erecinska, et al., "Regulation of GABA level in rat brain synaptosomes: Fluxes through enzymes of GABA shunt and effects of glutamate, calcium, and ketone bodies," *J. Neurochem.* 67:2325–2334 (1996).

Seebach, et al., "176. Preparation and structure of oligolides from (R)–3–hydroxypentanoic acid and comparison with the hydroxybutanoic–acid derivatives:A small change with large consequences," *Helvetica Chimica Acta* 77:2007–34 (1994).

Tasaki, et al., "The dimer and trimer of 3–hydroxybutyrate oligomer as a precurser of ketone bodies for nutritional care," *Journal of Parenteral and Enteral Nutrition* 23:321–325 (1999).

* cited by examiner

NUTRITIONAL AND THERAPEUTIC USES OF 3-HYDROXYALKANOATE OLIGOMERS

CROSS-REFERENCE TO RELATED APPLICATIONS

Priority is claimed to U.S. provisional application Ser. No. 60/093,760, filed Jul. 22, 1998.

BACKGROUND OF THE INVENTION

The present invention is generally in the field of nutritional and therapeutic compositions for the modulation of ketone levels in humans and other mammals.

There are a number of conditions in human and animals in which it is desirable to increase the levels of ketone bodies in the human or animal body. Examples include seizure control, treatment of certain metabolic disorders, reduction of protein catabolism, appetite suppression during weight loss, and parenteral nutrition.

A number of treatments exist for seizure control in epileptic patients. Anti-seizure medications are popular; however, they are not always effective and can cause undesirable side-effects. A ketogenic diet has been used since the turn of the century, but lost favor with the development of anti-seizure medications. The ketogenic diet recently has attracted new interest for the treatment of certain forms of epilepsy, as well as other medical conditions. The diet, which typically is carefully controlled and doctor supervised, is very high in fat calories and low in carbohydrates. The diet forces the body to metabolize fats instead of carbohydrates for energy, thereby elevating the level of acetoacetate and D-3-hydroxybutyrate in the blood. These compounds are referred to as "ketone bodies," thus the term "ketogenic" is used to describe the diet.

While the exact mechanism of action of the ketogenic diet is not well understood, it is believed that the elevated blood levels of ketone bodies have sedative effects which help to prevent seizures. In order to be effective for this purpose, however, the patient must strictly observe the diet. Vitamin and mineral supplements are included in the diet to make it nutritionally complete, since the diet is very high in fat, low in proteins, and requires the near elimination of carbohydrates. Each patient's diet is mathematically calculated based on the age, size, and activity level of the patient. Patients normally follow the diet for one to two years, at which time the patient is slowly weaned onto a normal diet. The diet has been found to be particularly effective with epileptic children. Major drawbacks are that the diet is not very palatable and that patient compliance demands complete commitment on the part of the patient and his or her family. Moreover, the diet's high fat content can increase the risk of vascular diseases, such as atherosclerosis.

Special diets are also used when a person urgently needs to lose weight for health reasons, for example prior to surgery or due to complications from obesity. In this situation, the doctor may prescribe a diet greatly restricting the person's caloric intake. With the caloric intake reduced, the body is forced to metabolize storage reserves for energy. The body can derive energy from fat and skeletal tissue, such as muscle and proteins. It is preferable, however, that fat tissue be used rather than protein, since the breakdown of proteins (i.e. "catabolism") can undesirably result in muscular atrophy, immuno-suppression, and reduced wound healing. Supplementation of the diet with hydroxybutyric acid has been shown to reduce protein catabolism in subjects on low energy diets (Pawan & Semple, *Lancet* 8:15 (1983)). It also has been reported that 3-hydroxybutyrate beneficially suppresses the appetite.

Total parenteral nutrition ("TPN") is used to provide nutrients to patients who are unable to ingest food orally, such as in the case of intestinal failure. Common causes of this condition include inflammatory disorders of the gastrointestinal tract (e.g., Crohn's disease), radiation enteritis, and short bowel resulting from surgical resection of necrotic or diseased bowel. Approximately 22,000 outpatients and 150,000 inpatients currently receive TPN in the United States alone (*PR Newswire: Orphan Medical Announcement*, Jun. 9, 1995). Patients receive the nutrients, which typically are concentrated fat emulsions, directly into their veins. The nutrient compositions are described, for example, in U.S. Pat. No. 4,563,354 to Chang et al.; EP 0321428 A1; U.S. Pat. No. 5,093,044 to Wretlind et al.; PCT WO 88/08301; PCT WO 90/02548; PCT WO 90/02549; and PCT WO 90/11753. Parenteral treatment with fat emulsions, however, can have serious side effects, such as catheter obstruction, hyperlipemia, thrombopathy, fat overload syndrome, and fat embolism (Desrochers, et al., *J. Nutr. Biochem.* 6:111–18 (1995)). It would therefore be tremendously beneficial to develop high energy, water soluble nutrients which can be used for long-term intravenous feeding.

In principle, the ketone bodies R-3-hydroxybutyrate and acetoacetate, which are natural constituents of human sera, could be used for intravenous feeding in lieu of fat emulsions. These compounds are good fuels for peripheral tissues, except during prolonged starvation and diabetic ketoacidosis, and are ultimately oxidized to carbon dioxide. Unfortunately, administration of these compounds in their acid form can cause vein irritation, and infusion of the compounds as sodium salts can result in a dangerous sodium overload (Desrochers, et al., *J. Nutr. Biochem.*, 6:1 11–18 (1995)). To overcome these problems, researchers have explored the administration of R-3-hydroxybutyrate with other basic amino acid salts (Beylot et al., *Crit. Care Med.* 22:1091–98 (1994); Lammerant, et al., *J. Mol. Cell. Cardiol.* 17:421–33 (1985)). Such treatments, however, may interfere with the transport of amino acids across the blood-brain barrier and/or harm patients with hepatic or renal pathologies (Desrochers, et al., *J. Nutr. Biochem.* 6:111–18 (1995)). Others have described the use of sodium salts of 3-hydroxybutyric acid oligomers as nutrients, in order to decrease the ratio of salt to ketone body (Japanese Patent No. 94,321,778 to Hiraide, et al.).

Another approach utilizing a ketone body as a nutrient focuses on the synthesis of a glycerol monoester of acetoacetate, which is hydrolyzed in plasma and tissues to glycerol and acetoacetate (Birkhahn & Border, *Am. J. Clin. Nutr.* 3:436–41 (1978); Birkhahn, et al., *J. Nutr.* 109:1168–74 (1979)). This composition was first to provide administration of large amounts of a ketone body without a large sodium load.

Researchers also have explored using precursors to the ketone bodies. For example, R, S-1,3-butanediol is a water soluble precursor, which is metabolized in the liver to R, S-3-hydroxybutyrate (Desrochers, et al., *J. Nutr. Biochem.* 6:111–18 (1995)). However, the diol is unsuitable for use as an intravenous nutrient because it has a low caloric density per osmol, and because its oxidation in the liver markedly increases the [NADH]/[NAD$^+$] ratio, which can induce alcoholic hypoglycemia. One effort to address these problems has focused on using an acetoacetate ester of R, S-1,3-butanediol, so that acetoacetate liberated by esterases can trap the reducing equivalents generated in the liver by the oxidation of the diol (Desrochers, et al., *J. Nutr. Biochem.* 6:111–18 (1995)).

Modulating ketone body levels also is useful in the production of animals for the meat industry. U.S. Pat. Nos. 4,329,359 and 4,423,072 to Stahly disclose feeding dihydroxyalkanols and triglycerides to pregnant sows to improve the metabolic stability of newborn pigs. These compositions function to increase the ketone body levels in the sow. The ketone bodies then are transferred across the placenta, providing a supplemental energy source to the developing fetus.

PCT WO 98/41200 and PCT WO 98/41201 by British Technology Group Ltd disclose the use of acetoacetate in combination with poly D-β-hydroxybutyrate or esters or oligomers thereof, and/or a metabolic precursor or salt thereof in nutritional or therapeutic compositions to elevate the levels of ketone bodies in the blood for increasing cardiac efficiency, treatment of diabetes and insulin resistant states, and treatment of effects of neurodegenerative disorders and epilepsy. Although these applications provide mechanisms by which the ketone levels can be elevated for treatment of these disorders, the number of useful composition is limited to acetoacetate in combination with either a precursor of, or oligomer or ester of, D-β-hydroxybutyrate.

It is therefore an object of the present invention to provide improved or alternative compositions for elevating ketone levels in the body of humans and other mammals, which are suitable for oral or parenteral administration.

It is a further object of the present invention to provide compositions having better or longer bioavailability, or different metabolic products, and methods of use thereof for seizure control, metabolic disease control, reduction of protein catabolism, appetite suppression, parenteral nutrition, increasing cardiac efficiency, treatment of diabetes, treatment of effects of neurodegenerative disorders or other conditions affecting or effected by ketone level in humans and other mammals.

SUMMARY OF THE INVENTION

Nutritional or therapeutic compositions are provided for increasing ketone body levels in the blood of mammals by providing a source of ketone bodies in the form of linear or cyclic oligomers and/or derivatives of 3-hydroxyacids. The 3-hydroxyacid can be in the form of a linear oligomer of 3-hydroxyacids other than linear homo-oligomers of 3-hydroxybutyric acid if administered in combination with acetoacetate, cyclic oligomers of 3-hydroxyacids, esters of the linear or cyclic oligomers, esters of 3-hydroxyacids other than 3-hydroxybutyric acid, and combinations thereof. An oligomer generally refers to a polymer of three or more hydroxyacids. Preferred 3-hydroxyacids include 3-hydroxybutyrate, 3-hydroxyvalerate, 3-hydroxyhexanoate, and 3-hydroxyheptanoate. Oligomers of odd-carbon number 3-hydroxyacids such as 3-hydroxyvalerate have advantages since they have a higher energy content than oligomers of 3-hydroxyacids having an even-number of carbons. The cyclic oligomers have advantageous properties since they result in a sustained, and/or controlled, ketone blood level over a period of hours.

The compositions can be administered orally, for example, as a nutritional or dietary supplement, or intravenously. Increasing blood ketone levels is useful for seizure control, metabolic disease control, reduction of protein catabolism, appetite suppression, parenteral nutrition, increasing cardiac efficiency, treatment of diabetes and insulin resistant states, and treatment of effects of neurodegenerative disorders and epilepsy.

DETAILED DESCRIPTION OF THE INVENTION

Figure 1:
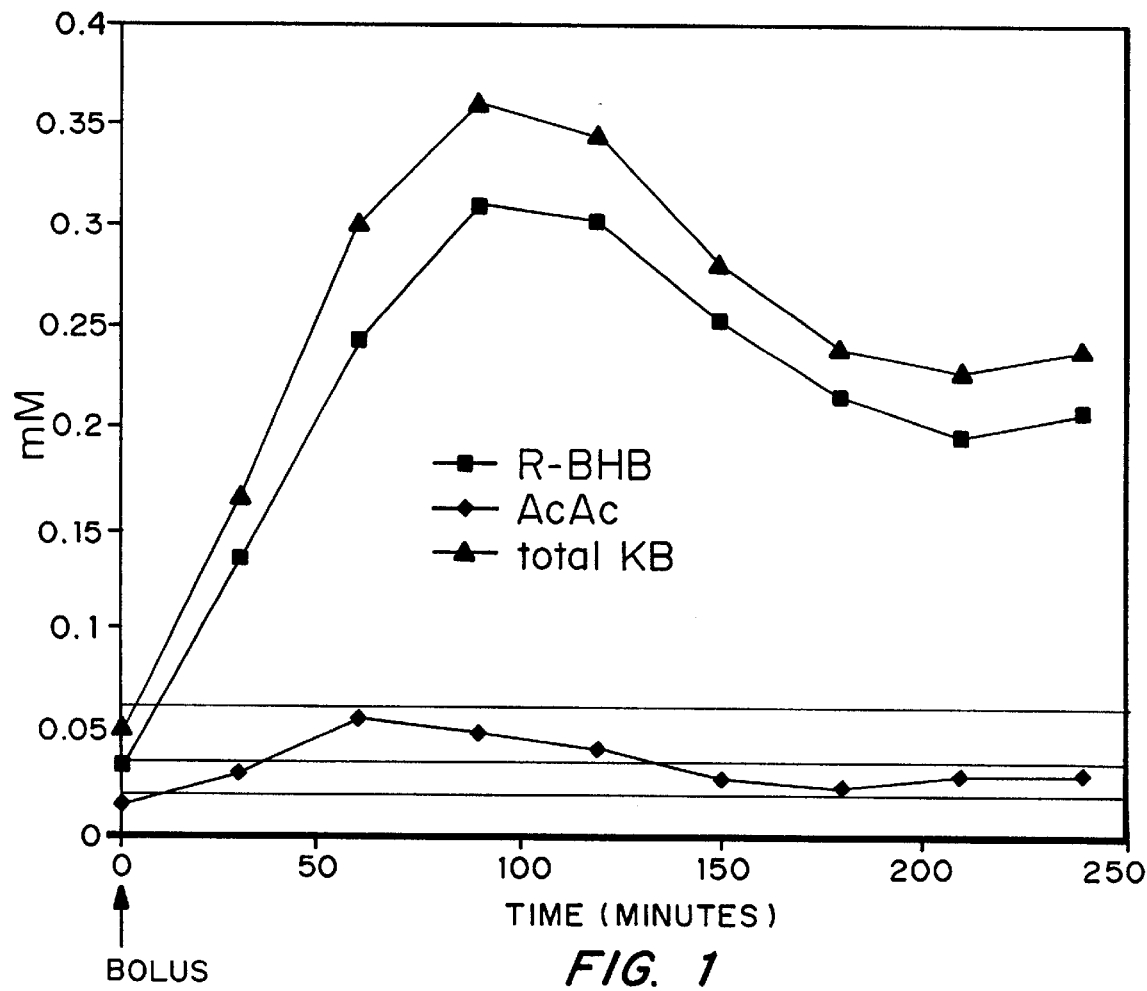
FIG. 1 is a graph of plasma total ketone bodies (mn) from a dog given a single oral bolus of triolide at 5% of the daily caloric requirement, over time in minutes, for R-BHB (squares), acetoacetate (diamonds, control), and total ketone bodies (triangles).

It was discovered that certain hydroxyacids, derivatives, oligomers and esters thereof, can provide a source of ketone bodies to modulate ketone body levels in the blood of mammals, and that biologically produced polyhydroxyalkanoates are an excellent source for these hydroxyacids. These oligomers and/or derivatives of 3-hydroxyacids can be readily adapted to produce a variety of nutritional and therapeutic compositions, without the drawbacks associated with known methods and compositions for elevating ketone levels.

I. Nutritional and Therapeutic 3-Hydroxyacids Compositions

The compositions include 3-hydroxyacids, linear or cyclic oligomers thereof, esters of the 3-hydroxyacids or oligomers, derivatives of 3-hydroxyacids, and combinations thereof. In one preferred embodiment, the compositions include the cyclic macrolide of R-3-hydroxyacids containing 3, 4, or 5 monomeric subunits. Preferred 3-hydroxyacids include 3-hydroxybutyric acid, 3-hydroxyvaleric acid, 3-hydroxyhexanoic acid and 3-hydroxyheptanoic acid. The preferred length of the oligomer must be such that the derivative has a suitable digestion rate for sustained release of monomer. In another preferred embodiment, the cyclic trimer (triolide) is used in a combination with other cyclic oligolides or linear esters and/or mixtures of both.

The general formula for 3-hydroxyacids is:

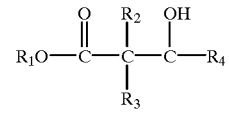

Where:
R$_1$ is selected from hydrogen, methyl, alkyl, alkenyl, aryl, arylalkyl, heteroalkyl, heteroaryl, thiol, disulfide, ether, thiolether, amine, amide, halogen, R$_2$ and R$_3$ are independently selected from hydrogen, methyl, alkyl, alkenyl, aryl, arylalkyl, heteroalkyl, heteroaryl, thiol, disulfide, ether, thiolether, amine, amide, halogen, hydroxy, ester, nitrogen-substituted radicals, and/or oxygen-substituted radicals.

R$_4$ is selected from hydrogen, alkyl, alkenyl, aryl, arylalkyl, heteroalkyl, heteroaryl, thiol, disulfide, ether, thiolether, amine, amide, halogen, hydroxy, ester, nitrogen-substituted radicals, and/or oxygen-substituted radicals.

further, when R$_4$ is not hydrogen or a halogen, R$_3$ can be a direct bond to R$_4$ and R$_4$ can be methyl.

The following definitions may be used through the specification.

The term "alkyl" refers to C$_{2-15}$ straight, branched or cyclic alkyl groups.

The term "alkenyl" refers to a branched or straight chain C$_2$–C$_{??(15)}$ hydrocarbon which also comprises one or more carbon-carbon double bonds.

The term "aryl" refers to a group a group containing one or more aromatic rings. Aryl groups can be unsubstituted or substituted with substituents independently selected from alkyl, haloalkyl, alkoxy, amino, alkyl amino, dialkylamino, hydroxy, halo, and nitro.

The term "arylalkyl" refers to an alkyl group (as defined above) to which is appended an aryl group.

The term "heteroalkyl" refers to an alkyl group (as defined above) wherein one or more of the carbon atoms is replaced with a non-carbon atom (such as, for example, oxygen, nitrogen, sulfur).

The term "heteroaryl" refers to a group containing one or more aromatic rings wherein at least one of the atoms in an aromatic ring in not carbon. Heteroaryl groups can be unsubstituted or substituted with substituents independently selected from alkyl, haloalkyl, alkoxy, amino, alkylamino, dialkylamino, hydroxy, halo and nitro.

The term "thiol" refers to RSH where R is alkyl, alkenyl, aryl, arylalkyl, heteroalkyl, or heteroaryl (as defined above).

The term "disulfide" refers to groups containing a sulfur-sulfur bond.

The term "ether" refers to groups containing a C—O—C unit.

Hydroxyacid Oligomers

In one preferred embodiment, the compositions include linear oligomers of 3-hydroxyacids having from 5 to 10 carbon atoms. As used herein, the term "oligomer" means a polymer having a weight average molecular weight of less than about 2000 g/mol, preferably less than about 1000 g/mol, or having less than about 100 monomeric subunits. Representative examples include oligomers of 3-hydroxyvalerate, 3-hydroxyhexanoate, 3-hydroxyheptanoate, 3-hydroxyoctanoate, and combinations thereof. As used herein, a homo-oligomer includes only one type of 3-hydroxyacid, while an oligomer can refer to either a homo-oligomer or hetero-oligomer including more than one type of 3-hydroxyacid.

In another preferred embodiment, the compositions include 3-hydroxyacids having an odd number of carbons, which have a higher caloric value than 3-hydroxyacids having an even number of carbons. For example, oligomeric esters of 3-hydroxyvalerate (alone or mixed with other hydroxyalkanoates) can be used to deliver the odd numbered hydroxyacid 3-hydroxyvalerate.

In still another preferred embodiment, the compositions include cyclic oligomers of 3-hydroxyalkanoic acids or 3-hydroxyalkanoate oligomer esters, including 3-hydroxyacids of from 4 to 10 carbon atoms. The hydroxyacids are liberated as a result of digestion or metabolism of the ester form. By providing the hydroxyacids in ester form, these compositions can eliminate complications caused by delivery of the acid or salt forms of hydroxyalkanoic acids.

As demonstrated by the following examples, cyclic oligomers have the advantage that the ketone body levels remain elevated for a prolonged period of time of at least several hours after ingestion. For example, cyclic esters of 3-hydroxybutyrate, such as the triolide of 3-hydroxybutyrate, can provide sustained release of ketone bodies. Slow release provides a major advantage over prior art compositions, since the slow release of monomers provides a more constant level of ketone bodies, such as 3-hydroxybutyrate, to the body over a prolonged period of time. This release profile reduces the frequency of doses required to maintain a specific ketone body concentration, which is especially important during periods, such as during sleep, when it is difficult to administer the material.

Derivatized HydroxyAcids

Since the family of PHAs contains a large variety of hydroxyacids with varying side chain substituents, judicious selection of the type of 3-hydroxyacids provides a means to increase the caloric density on a per acid basis or to provide acids with odd number chain lengths. Preferred derivatives are where the R groups on the formula shown above are ethyl or methyl.

Esters of 3-Hydroxyacids or Oligomers

The compositions also can include esters of 3-hydroxyacids or esters of either linear or cyclic 3-hydroxyacid oligomers. In another preferred embodiment, the compositions include R-3-hydroxyalkanoate oligomers terminated with an ester linkage, for example, to 1,3-butanediol. The length of the oligomer preferably is such that the derivative has a solubility suitable for intravenous administration. The 1,3-butanediol may be coupled to the hydroxyacid oligomer by the primary alcohol, the secondary alcohol, and/or mixtures of both. Following parenteral (e.g., intravenous) administration of the oligomer esters, the non-R-3-hydroxyacid units should be readily tolerated and metabolized in the body after it is released from the oligomer derivative.

The hydroxyacid oligomer also preferably is selected to include desirable physical and nutritional properties, such as water solubility and calorific benefits.

Sources of the Hydroxyacid Compositions

A useful source of hydroxyacids and hydroxyacid oligomers is the family of microbial storage polyesters, the polyhydroxyalkanoates, which can be accumulated intracellularly by numerous microorganisms. Poly [(R)-3-hydroxyalkanoates] (PHAs) are biodegradable and biocompatible thermoplastic materials, produced from renewable resources, with a broad range of industrial and biomedical applications (Williams & Peoples, *CHEMTECH* 26:38–44 (1996)).

In recent years, the PHA biopolymers have emerged from what was originally considered to be a single homopolymer, poly-3-hydroxybutyrate (PHB), into a broad class of polyesters with different monomer compositions. To date around 100 different monomers have been incorporated into the PHA polymers (Steinbüchel & Valentin, *FEMS Microbiol. Lett.* 128:219–28 (1995)). As described herein, these naturally occurring polyesters can be converted into derivatives suitable for nutritional and therapeutic uses.

Methods for Making the Hydroxyacid Oligomers and Derivatives

Representative methods for preparing the hydroxyacid oligomer derivatives described herein include direct degradation of polyhydroxyalkanoates to oligomeric derivatives; ring-opening of cyclic oligomers of 3-hydroxyalkanoates; polymerization of hydroxyalkanoates or derivatives thereof; and, stepwise synthesis hydroxyalkanoate oligomers beginning or ending with modification of a terminal hydroxyalkanoate unit. Such syntheses can be readily carried out using methods known in the art. In a preferred embodiment of the methods for synthesis of hydroxyacid oligomers terminated with an ester linkage to an alcohol, the process includes direct degradation of polyhydroxyalkanoate with the alcohol; ring-opening of a cyclic oligomer of hydroxyalkanoate with an alcohol; and, stepwise synthesis of hydroxyalkanoate oligomers beginning or ending with esterification of a terminal hydroxyalkanoate unit by an alcohol. Such syntheses can be carried out using methods known in the art.

Cyclic oligolides of (R)-3-hydroxybutyric acid can be prepared by a number of known methods, which are described, for example, in Seebach, et al., *Angew. Chem. Int. Eng. Ed.*, 4:434–35 (1992); Seebach, et al., *Helv. Chim. Acta.*, 71:155–67 (1988); Seebach, et al., *Helv. Chim. Acta.* 72:1704–17 (1989); and Mueller, et al., *Chimia* 45:376 (1991). These methods involve conversion from the bacterially-derived polyester, poly-(R)-3-hydroxybutyrate (PHB), or macrolide formation from the constituent acid (R)-3-hydroxybutyrate or esters thereof. The most direct route is degradation of PHB under acid catalyzed conditions to a mixture of linear oligomers and cyclic oligolides. Oligolides and oligomers can be isolated from the crude mixture via conventional washing, extraction, and distillation steps to yield purified materials.

II. Nutritional and Dietary Compositions

The compositions can be adapted for enteral or parenteral administration, for example, by combining the composition with the appropriate delivery vehicle. For enteral administration, the compositions can be added to food or drink, for example, as a dietary supplement. Alternatively, the compositions can be delivered parenterally, for example, by dissolving in a physiological saline solution for injection. Using genetic engineering techniques, plants can be engineered to express the appropriate 3-hydroxyacids or oligomers of 3-hydroxyacids. Suitable means and methods are described in WO97/15681 and PCT/US99/04999 by Metabolix.

The hydroxyacid formulations can be administered alone, in dry or powdered form, in solution in a carrier such as water, normal saline, or phosphate buffered saline, or mixed with other materials which will elevate blood ketones, such as free fatty acids, triglycerides alone or in combination with protein or carbohydrate. Traditional ketogenic diets, such as the diet recommended by the Marriott Corp. Health Care Services, Pediatric Diet Manual, Revised August 1987, contains from 3:1 to 4:1 g of fat for each g of combined carbohydrate and protein. Since the fat is metabolized to yield 3-hydroxyacid and acetoacetate, and desired levels are in the range of at least about 1 to 2 mM up to a maximum of about 7.5 mM (achieved during prolonged fasting of obese individuals), although ranges can be from 0.3 to 20 mM, the compositions containing the 3-hydroxyacids can be formulated to yield similar values to those of the traditional ketogenic diets, recognizing that the yield will be more efficient when the 3-hydroxy acids are administered directly.

These compositions can be mixed with meat or carbohydrate, as demonstrated in the examples, preferably maintaining an excess of 3-hydroxy acid relative to the amount of carbohydrate or protein.

III. Applications of the Compositions

The compositions described herein can readily be used in a variety of nutritional and therapeutic applications. One of skill in the art can readily select the appropriate hydroxyacid oligomer or derivative, as well as amounts thereof, for administration. The particular composition used will depend on the target ketone blood levels (required for a particular patient), as well as the route and frequency of administration. In all cases, the digestion and metabolism of these compounds advantageously provides for the slow release of ketone bodies.

Representative uses for the compositions described herein are provided below:

Using the hydroxyacid oligomer derivatives described herein, it is possible to sustain ketosis while overcoming drawbacks of the ketogenic diet. During normal digestion and metabolism of these compounds, ketone bodies (such as 3-hydroxybutyrate and acetoacetate) are released into the blood. The blood level of ketone bodies can be maintained at a level necessary to produce ketosis and reduce seizures, which for example, are associated with epilepsy.

The hydroxyacid oligomer derivatives described herein can also be administered to maintain the blood level of ketone bodies at a level necessary to reduce protein catabolism and provide appetite suppression, to aid in weight loss. Thus, addition of these ketogenic compounds to the diet functions to mimic some effects of a ketogenic diet. Preferred blood levels to be obtained are in the range of 2 to 3 mM 3-hydroxyacid. The caloric value of the ketone bodies is approximately 1.5 g of ketone/e g of fat. The hydroxyacid oligomer derivatives described herein can be administered parenterally to a mammal, typically a human, to maintain the blood level of ketone bodies at a level necessary to provide nutrients to the body. The compositions should be particularly useful to patients who are unable to digest food orally or otherwise require total parenteral nutrition. The compositions can be formulated to provide high energy, water soluble nutrients, suitable for long-term intravenous feeding.

The hydroxyacid oligomer derivatives described herein can be administered to maintain the blood level of ketone bodies at a level necessary to overcome deficiencies caused by metabolic disorders, such as insulin deficiencies or insulin resistant states. The hydroxyacid oligomer derivatives described herein can be administered to maintain the blood level of ketone bodies at a level necessary to treat insulin resistance in which the normal insulin signaling pathways is disordered and in conditions in which cardiac (hydraulic work) efficiency is reduced due to metabolic reasons, as described in PCT WO 98/41200 and PCT WO 98/41201, which are incorporated herein by reference.

The hydroxyacid oligomer derivatives described herein can also be administered to a mammal, typically a human, to maintain the blood level of ketone bodies at a level necessary to treat a variety of neurodegenerative diseases, particularly those involving neurotoxic plaques, such as amyloid plaques. Examples of neurodegenerative diseases which the compositions described herein may aid in treating include Alzheimer's disease, fronto-temporal degeneration associated with Pick's disease, vascular dementia, senile dementia of Lewy body type, dementia of Parkinsonism with frontal atrophy, progressive supranuclear palsy and corticobasal degeneration, Downs syndrome associated Alzheimer's, myasthenia gravis, and muscular dystrophy. See, for example, PCT WO 98/41200 and PCT WO 98/41201 by British Technology Group, Ltd., which discloses that elevated levels of ketone bodies can improve nerve cell function and growth, at least in part by enhancing cellular energy production. The preferred ketone blood level for treatment of neurodegenerative disorders is greater than for diet or seizures, more typically in the range of 7.5 mM.

Supplemental Energy Source for Livestock

The hydroxyacid oligomer derivatives described herein can be administered to animals, such as pigs, particularly pregnant sows, to provide a supplemental energy source and to possibly improve the metabolic stability of newborn animals. For example, by increasing the ketone body levels in a pregnant sow, ketone bodies are transferred across the placenta, providing a supplemental energy source to the developing fetus.

The compositions and methods described herein are further described by the following non-limiting examples.

EXAMPLE 1

Preparation of (R,R,R)-4,8,12-Trimethyl-1,5,9-Trioxadodeca-2,6,10-Trione or Triolide of (R)-3-Hydroxybutyric Acid PHB (20 g) was dissolved in dioxane (700 mL) containing p-toluene sulfonic acid monohydrate (4 g) and concentrated sulfuric acid (5 mL). After refluxing for 4 days, the reaction had achieved 40% conversion to the triolide, as determined by gas chromatography (GC) analysis (Riis & Mai, *J. Chromatography* 4:285–89 (1988)). The reaction mixture was cooled to room temperature and quenched with saturated sodium bicarbonate solution. Dioxane was removed by rotary evaporation. The residue was extracted into ethyl acetate (400 mL), washed with brine, and concentrated to an oil. Vacuum distillation yielded purified triolide (4 g).

EXAMPLE 2

Use of 3-Hydroxyalkanoic Acid Oligolide for Enteral Nutrition

A mongrel dog (21 kg) was fasted overnight and given an oral bolus of triolide (R,R,R)-4,8,12-trimethyl-1,5,9-trioxadodeca-2,6,10-trione, 10 g) in gelatin. This amount of triolide is equivalent to 5% of the daily caloric requirement. Blood was sampled at 0, 15, 30, 45, and 60 minutes and every half hour thereafter for a total of six hours.

The blood samples were analyzed for glucose via enzymatic assay, and for acetoacetate and 3-hydroxybutyrate via GC-mass spectrometry (GC-MS) assay. As shown by FIG. 1, within 90 minutes, the blood concentrations of 3-hydroxybutyrate and acetoacetate reached 0.3 and 0.05 mM, and the total ketone bodies in the blood were 0.36 mM. After the fourth hour, the total ketone body concentration remained elevated at 0.24 mM. Glucose concentration in the blood dropped from 6.5 mM to 5 mM during the experiment.

These results show that an oral dose of a 3-hydroxyalkanoic oligolide can elevate the ketone body concentration in the blood. A significant finding is that the ketone body concentration remains elevated several hours after administration, demonstrating that the triolide is useful for the slow release of ketone bodies.

EXAMPLE 3

Use of 3-Hydroxyalkanoic Acid Oligolide for Enteral Nutrition

A mongrel dog (25.5 kg) was fasted overnight and fed a mixture of meat (111 g) and triolide ((R,R,R)-4,8,12-trimethyl-1,5,9-trioxadodeca-2,6,10-trione, 23.5 g). This amount of triolide is equivalent to 10% of the daily caloric requirement. Identical amounts of meat and triolide were given at 0, 120, 360 and 540 minutes. Blood was sampled at regular intervals for 12 hours.

Throughout the experiment, the dog exhibited no signs of distress; unusual behavior; or abnormal bodily functions, such as diarrhea, nausea, vomiting, or frequent urination. The blood samples were analyzed for acetoacetate and 3-hydroxybutyrate. Within 30 minutes, the concentrations of 3-hydroxybutyrate and acetoacetate reached 0.85 and 0.15 mM, respectively. The total ketone bodies in the blood were 1.0 mM. After the third feeding of triolide, total ketone body concentration remained elevated and steady at about 0.6 mM. Glucose concentration in the blood remained within the normal range of 3.1 to 5.9 mM. Other clinical chemistry profiles remained normal throughout the experiment. By the next morning, the ketone body concentration in the blood had returned to the normal value of 0.02 mM.

These results show that triolide is digested by the dog, resulting in a sustained increased in blood ketone body concentration. Significantly, the ketone body concentration is within the range achieved by the ketogenic diet used in the nutritional treatment of intractable epilepsy. Furthermore, the triolide was found to be well accepted by the dog, which showed no sign of distress and no perturbation of clinical chemistry parameters. These results further demonstrate that the triolide is useful for the slow release of ketone bodies.

EXAMPLE 4

Synthesis of an Alkyl Ester Terminated 3-Hydroxyalkanoate Oligomer

Oligomeric (R)-3-hydroxybutyrate was prepared via condensation reaction of methyl (R)-3-hydroxybutyrate. Specifically, methyl (R)-3-hydroxybutyrate (250 µl) was heated with dibutyltin oxide (2 mg) at 110° C. for 72 hours. The reaction vial was left open to the atmosphere to permit removal of methanol. After cooling, the reaction formed a crystalline, white solid material, which was washed with methanol and allowed to air dry. NMR analysis showed formation of oligomeric (R)-3-hydroxybutyrate having an approximate molecular weight of 1,700 g/mol. Gel permeation chromatography (GPC) analysis confirmed the Mw at about 2,000 g/mol. NMR analysis also demonstrated the presence of a terminal methyl ester.

EXAMPLE 5

Synthesis of a Butanediol Ester Terminated 3-Hydroxyalkanoate Oligomer

Oligomeric (R)-3-hydroxybutyrate butanediol ester was prepared via controlled transesterification of the microbial polyester, poly[(R)-3-hydroxybutyrate] with 1,3-butanediol. Specifically, PHB (10 g, Mw 600,000) was dissolved with heating in 200 mL of dioxane and 1,3-Butanediol (2.1 mL). After dissolution, the reaction mixture was cooled and concentrated sulfuric acid (1 mL) was slowly added. The reaction mixture was heated at reflux for 48 hours. Samples were removed periodically and precipitated into water. After 6 hours, 95% of the product was recovered, having a Mw of 4,300 Da according to GPC analysis. After 45 hours, 52% of the product was recovered, having a Mw of 2,000 Da according to GPC analysis. NMR analysis demonstrated a 3-hydroxybutyrate oligomer of approximately 1,000 g/mol and demonstrated the presence of a terminal 1,3-butanediol ester.

EXAMPLE 6

Synthesis of a 3-Hydroxyalkanoate Oligomer

Oligomeric (R)-3-hydroxybutyrate was prepared via controlled hydrolysis of the microbial polyester, poly[(R)-3-hydroxybutyrate]. Specifically, PHB (150 g) was dissolved with heating in 2 L of glacial acetic acid. Water (350 ml) was slowly added to the viscous solution to form a single phase. The reaction mixture was heated at reflux for 18 hours. After cooling to about 55° C., the mixture was poured with rapid stirring into 9 L of water. The white precipitate was collected and washed with water to yield 92 g of 3-hydroxybutyrate oligomer after drying. NMR analysis demonstrated a 3-hydroxybutyrate oligomer of approximately 1,000 g/mol, with no terminal crotonization. GPC analysis confirmed a molecular weight of 1,000 g/mol.

A similar process was used, but with the addition of hydrochloric acid, to produce 3-hydroxybutyrate oligomer of lower molecular mass (approximately 200 g/mol). Oligomeric (R)-3-hydroxyvalerate can be prepared using the same approach from poly(3-hydroxyvalerate) which can be obtained by fermentation using *Chromobacter violaceum* (Steinbuchel, et. al., *Appl. Microbiol. Biotechnol.* 39:443–49 (1993)).

EXAMPLE 7

Use of 3-Hydroxyalkanoic Oligomers for Enteral Nutrition

Sprague-Dawley rats were fed commercial rat chow for 10 days and then switched to a control diet containing 75% of the calories from starch, 20% as casein, and 5% as polyunsaturated oil, plus mineral mix and liver extract supplements. After 15 days, two groups of rats were fed an experimental diet containing 25% of the calories from a 3-hydroxybutyrate oligomer. Two different oligomers, short and medium, were used with molecular masses of either the 200 g/mol or 1000 g/mol, respectively. A control group was kept on the control diet without oligomer.

The weight of each rat was measured daily. Urine samples were collected daily and analyzed for 3-hydroxybutyrate by GC-MS. After 5 days on the experimental diet, the rats were euthanized, and a blood sample was collected and analyzed for 3-hydroxybutyrate and acetoacetate by GC-MS.

The weight of the control group increased uniformly throughout the experiment, as did the weight of rats fed the experimental diet containing the medium HB oligomer. The weight of rats fed the experimental diet containing short HB oligomer decreased slightly while on the experimental diet.

The concentration of ketone bodies in the rat blood plasma collected at time of euthanasia was measured by GC-MS. The control group showed normal concentrations of 3-hydroxybutyrate and acetoacetate, 0.07 and 0.02 mM, respectively. Rats fed the short HB oligomer had 3-hydroxybutyrate and acetoacetate concentrations of 0.65 and 0.05 mM, respectively, while rats fed the medium oligomer had concentrations of 0.15 and 0.04 mM, respectively. These result show that the rats fed 3-hydroxybutyrate oligomers had increased levels of ketone bodies in their blood.

The concentration of 3-hydroxybutyrate in the urine of rats fed short and medium oligomers was determined by GC-MS to be approximately 3.5 and 1.0 mM, respectively. 3-Hydroxybutyrate was undetectable in the urine of the control rats. These results show that an oral dose of 3-hydroxybutyrate oligomers elevates the ketone body concentration in the blood and in the urine.

Modifications and variations of the present invention will be obvious to those of skill in the art from the foregoing detailed description. Such modifications and variations are intended to come within the scope of the following claims.

We claim:

1. A method of modulating blood ketone levels in a mammal, comprising administering to a mammal in which said modulation is intended a nutritional or therapeutic dietary composition comprising an effective and biocompatible amount of a 3-hydroxyacid derivative selected from the group consisting of linear oligomers of 3-hydroxyacids, other than linear homo-oligomers of 3-hydroxybutyric acid; cyclic oligomers of 3-hydroxyacids; esters of 3-hydroxyacids, other than 3-hydroxybutyric acid or linear homo-oligomers of 3-hydroxybutyric acid; esters of linear or cyclic 3-hydroxyacid oligomers other than linear homo-oligomers of 3-hydroxybutyric acid; and combinations thereof; wherein when the 3-hydroxyacid derivative is a linear oligomer of a 3-hydroxyacid or an ester of a 3-hydroxyacid, said 3-hydroxyacid derivative is administered in combination with acetoacetate.

2. The method of claim 1 wherein the blood ketone level is effective to control seizures.

3. The method of claim 1 wherein the blood ketone level is effective to control metabolic disorders of ketone body synthesis and metabolism.

4. The method of claim 1 wherein the blood ketone level is effective to reduce protein catabolism in and/or suppress the appetite of the mammal.

5. The method of claim 1, wherein the blood ketone level is effective to increase the cardiac efficiency of the mammal.

6. The method of claim 1, wherein the blood ketone level is effective to treat diseases selected from the group consisting of diabetes and other insulin resistant states in which the normal insulin signaling pathways are disordered, neurodegenerative diseases, and epilepsy.

7. The method of claim 1, wherein the mammal is a human or livestock animal.

8. The method of claim 1, wherein the composition is administered parenterally.

9. The method of claim 1, wherein the composition is administered orally as a dietary or nutritional composition.

10. A method of treating a neurodegenerative disorder in a mammal in need thereof, comprising administering to the mammal a nutritional or therapeutic dietary composition comprising an effective and biocompatible amount of a 3-hydroxyacid derivative selected from the group consisting of linear oligomers of 3-hydroxyacids other than linear homo-oligomers of 3-hydroxybutyric acid in combination with acetoacetate; cyclic oligomers of 3-hydroxyacids; esters of 3-hydroxyacids, other than 3-hydroxybutyric acid or linear homo-oligomers of 3-hydroxybutyric acid in combination with acetoacetate; and esters of 3-hydroxyacid linear or cyclic oligomers other than linear homo-oligomers of 3-hydroxybutyric acid in combination with acetoacetate; and combinations thereof.

11. The method of claim 10, wherein, following said administration, the resulting blood ketone level is effective to increase the cardiac efficiency of the mammal.

12. The method of claim 10, wherein the neurodegenerative disorder is selected from the group consisting of Alzheimer's disease, fronto-temporal degeneration associated with Pick's disease, vascular dementia, senile dementia of the Lewy body type, dementia of Parkinsonism with frontal atrophy, progressive supranuclear palsy and corticobasal degeneration, Down's syndrome associated with Alzheimer's, myasthenia gravis, and muscular dystrophy.

* * * * *